United States Patent [19]
Nakatsuka et al.

[11] Patent Number: 4,970,021
[45] Date of Patent: Nov. 13, 1990

[54] PHTHALOCYANINE COMPOUNDS AND UTILITY THEREOF

[75] Inventors: Masakatsu Nakatsuka; Tsutomu Nishizawa; Takahisa Oguchi; Hisato Itoh, all of Yokohama; Katashi Enomoto, Zushi, all of Japan

[73] Assignees: Mitsui Toatsu Chemicals, Incorporated, Tokyo; Yamamoto Chemicals, Incorporated, Yao, both of Japan

[21] Appl. No.: 237,419

[22] Filed: Aug. 29, 1988

[30] Foreign Application Priority Data

Aug. 31, 1987 [JP] Japan ............................ 62-215522
Dec. 28, 1987 [JP] Japan ............................ 62-329893

[51] Int. Cl.$^5$ ............... C09K 19/52; C09K 19/00; G03C 1/492; C09B 47/04
[52] U.S. Cl. ............... 252/299.01; 252/299.1; 252/299.3; 540/122; 540/139; 540/140; 430/270; 430/495; 430/944; 430/945
[58] Field of Search ............ 252/299.01, 299.1, 299.2, 252/299.3; 540/122, 139, 140; 430/270, 495, 944, 945, 496

[56] References Cited

U.S. PATENT DOCUMENTS

| | | | |
|---|---|---|---|
| 4,460,665 | 7/1984 | Kunikane et al. | 428/199 |
| 4,507,374 | 3/1985 | Kakuta | 540/122 |
| 4,537,713 | 8/1985 | Eckert | 540/139 |
| 4,555,463 | 11/1985 | Hor et al. | 540/140 |
| 4,622,179 | 11/1986 | EDA | 540/139 |
| 4,814,256 | 5/1989 | Aldag et al. | 540/140 |

FOREIGN PATENT DOCUMENTS

| | | |
|---|---|---|
| 20198140 | 10/1986 | European Pat. Off. . |
| 20213923 | 3/1987 | European Pat. Off. . |
| 1164234 | 9/1969 | United Kingdom ................ 540/122 |
| 2168372 | 6/1986 | United Kingdom . |

Primary Examiner—John S. Maples
Assistant Examiner—Philip Tucker
Attorney, Agent, or Firm—Oblon, Spivak, McClelland, Maier and Neustadt

[57] ABSTRACT

Phthalocyanine compounds are described, which are represented by the following general formula (I):

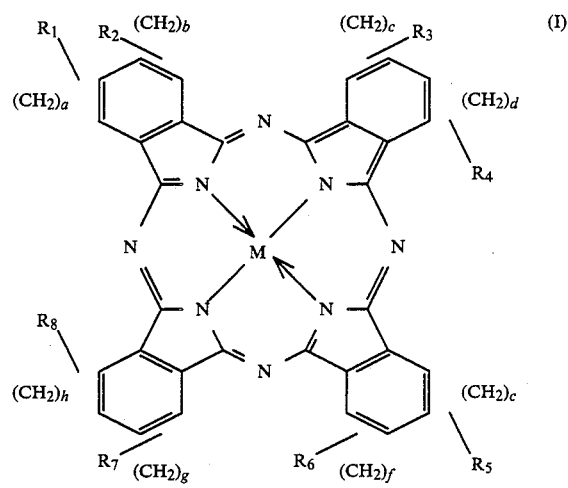

wherein $R_1$–$R_8$ are individually a hydrogen atom or an alkyl or aryl group, a–h stand individually for an integer of 1–20, and M denotes two hydrogen atoms or a metal atom, metal halide, metal oxide, metal hydroxide, dialkylmetal, diarylmetal, bis(alkyloxy)metal or bis(trialkylsilyloxy)metal. Optical recording media and liquid crystal display panels, which contain at least one of the phthalocyanine compounds, are also described.

3 Claims, 3 Drawing Sheets

PHTHALOCYANINE COMPOUNDS AND UTILITY THEREOF

BACKGROUND OF THE INVENTION (1) Field of the Invention

This invention relates to phthalocyanine compounds, and particularly to phthalocyanine compounds capable of showing absorption in the near infrared range.

(2) Description of the Related Art

Cyanine compounds, various metal compounds and the like have conventionally been known as absorptive materials in the near infrared and infrared range. These compounds are however generally unstable to light and heat.

On the other hand, phthalocyanine compounds are very stable to light, heat, moisture, etc. and have excellent fastness. Owing to their high stability and intense tones, they have been found wide-spread utility as various dyes or pigments. They are also interesting, for example, as materials for dark conduction, photoconduction or energy conversion, materials such as electrodes and catalysts, and high molecular materials suited for use in the production of films or thin films having a high-degree function when blended with a high molecular substance. A variety of investigation is hence under way in this respect. Such phthalocyanine compounds however have difficulties in forming them into films, especially, by spin coating, because their solubility in an organic solvent is low.

Liquid crystal displayers have been proposed, which make use of electro- and thermooptical effects of a liquid crystal having a smectic phase as a liquid-crystal material having thermooptical effects or electro- and thermooptical effects and permit input of information by a near infrared light source such as a light pen equipped with a semiconductor laser and electrical read-out of the information thus inputted.

In a displayer of the above-described type, positioning of a light pen on its liquid crystal display panel results in focusing of a laser beam on a heat-absorbing film on a heating electrode, so that localized generation of heat is induced and the heat is then conducted to a liquid-crystal material in the vicinity of the heat-absorbing film to heat the liquid-crystal material. The liquid-crystal material is tentatively transformed into an isotropic liquid phase in the above-described manner and after movement of the light pen, the thus-heated liquid-crystal material is allowed to cool back into the smectic phase again. Here, domains presenting strong scattering of light in the liquid crystal are formed.

It is hence possible to create a scattered state, in other words, to write or draw characters or a pattern in accordance with movement of the light pen.

This method is however accompanied by a drawback that the efficiency of heat utilization is low, since the heat generated in the heat-absorbing film must be conveyed to the liquid-crystal material by conduction so as to heat the liquid-crystal material. Large laser power has thus been needed for writing information.

As one method for eliminating this drawback, it has been proposed to mix a pigment capable of showing absorption near laser wavelengths (in the near infrared range) as disclosed in the article entitled "A Semiconductor Laser Addressed Dye Doped Liquid Crystal Light Valve" reported in Proc. of the 3rd International Display Research Conference, pp 486-489 (1984). This method has however not been practised because the pigments known to date are not satisfactory in their solubility in a liquid-crystal material and/or in their light fastness.

SUMMARY OF THE INVENTION

An object of this invention is to provide a phthalocyanine compound which has excellent weatherability and very high solubility in organic solvents and liquid crystals, permits formation of a film by spin coating and shows absorption in the near infrared range.

Another object of this invention is to provide an optical recording medium containing the phthalocyanine compound.

A further object of this invention is to provide a liquid crystal display panel which is free of the drawbacks mentioned above, allows low-energy writing and has a long service life.

The present inventors have proceeded with a wide variety of investigation with a view toward solving the above-described problems. As a result, the above objects of the present invention have been attained successfully by phthalocyanine derivatives having a specific chemical structure.

In one aspect of this invention, there is thus provided a phthalocyanine compound represented by the following general formula (I):

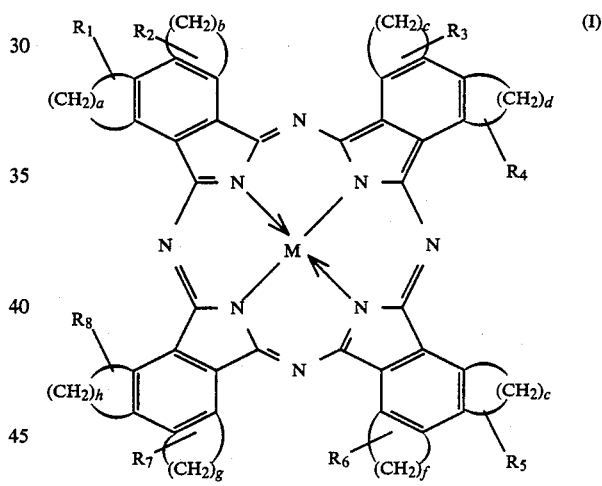

wherein $R_1-R_8$ are individually a hydrogen atom or an alkyl or aryl group, a–h stand individually for an integer of 1–20, and M denotes two hydrogen atoms or a metal atom, metal halide, metal oxide, metal hydroxide, dialkylmetal, diarylmetal, bis(alkyloxy)metal or bis(trialkylsilyloxy)metal.

In another aspect of this invention, there is also provided an optical recording medium comprising at least one phthalocyanine compound represented by the general formula (I).

In a further aspect of this invention, there is also provided a liquid crystal display panel composed of two substrates provided in combination with one side of one of said two substrates opposing one side of the other substrate, at least one electrode provided on each of the substrates and a liquid-crystal material having thermooptical effects or electro- and thermooptical effects and sealed between said two substrates, in which said liquid-crystal material comprises at least one phthalocyanine compound represented by the general formula (I).

The compounds according to the present invention have been found to be very useful as optical recording media for semiconductor lasers owing to their very high solubility in organic solvents and liquid crystals and their of absorption and reflection in the near infrared range.

Since the energy of light is absorbed in a light-absorptive substance of this invention mixed in a liquid-crystal material in a liquid crystal layer and heat is hence generated directly in the liquid crystal layer, the efficiency of utilization of the thermal energy is high so that faster writing of a thicker line is feasible at a smaller laser output.

In addition, the liquid crystal display panel according to this invention has excellent weatherability.

BRIEF DESCRIPTION OF THE DRAWINGS

The above and other objects, features and advantages of the present invention will become apparent from the following description and the appended claims, taken in conjuction with the accompanying drawings, in which:

DETAILED DESCRIPTION OF THE INVENTION AND PREFERRED EMBODIMENTS

Figure 1:
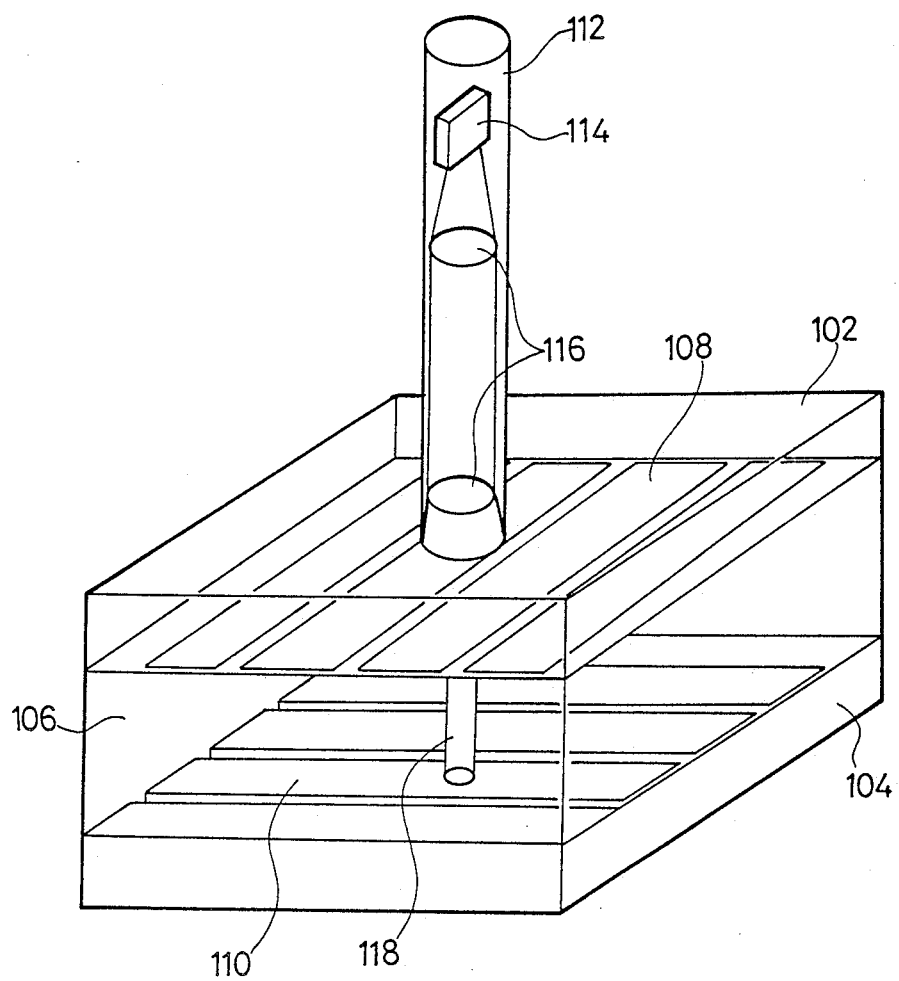
FIG. 1 is a schematic perspective view of a liquid crystal device including a liquid crystal display panel according to one embodiment of this invention and a light pen.

In the general formula (I) for the phthalocyanine compounds according to this invention, $R_1$–$R_8$ are individually a hydrogen atom or an alkyl or aryl group, preferably, a hydrogen atom or an alkyl group having 1–20 carbon atoms. The position of each alkyl group on its corresponding alicyclic ring is optional. a–h stand individually for an integer of 1–20, with an integer of 2–16 being preferred and an integer of 3–10 being particularly preferred. M denotes two hydrogen atoms or a metal atom, metal halide, metal oxide, metal hydroxide, dialkylmetal, diarylmetal, bis(alkyloxy)metal or bis(trialkylsilyloxy)metal, with two hydrogen atoms or a metal atom, metal halide, metal oxide, dialkylmetal or bis(trialkylsilyloxy)metal being preferred and two hydrogen atoms or a metal atom, metal oxide or dialkylmetal being especially preferred. As specific examples of the metal atom, may be mentioned Ni, Cu, Zn, Co, Fe and the like. VO and the like may be mentioned as exemplary metal oxides, while dialkylsilicons and the like may be mentioned as illustrative examples of the dialkylmetal.

The compounds according to this invention can each be prepared by a process known per se in the art, for example, using as a starting material a 1,2-dicyanobenzene derivative, phthalic acid derivative or phthalic anhydride or a diiminoisoindoline derivative available readily from its corresponding 1,2-dicyanobenzene derivative.

When cyclization is effected for the preparation of a phthalocyanine compound by using a compound having a substituent group on its alicyclic structure, the phthalocyanine compound is usually formed as a mixture of isomers having the substituent group at different positions on the alicyclic structure. Only major one of the components of such a mixture will however be referred to for the sake of convenience in this specification.

Representative compounds of this invention will be listed hereinafter.

Illustrative Compound No.

1

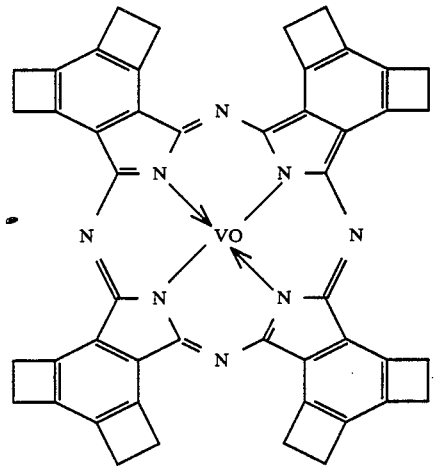

-continued
| | Illustrative Compound No. |
|---|---|
| 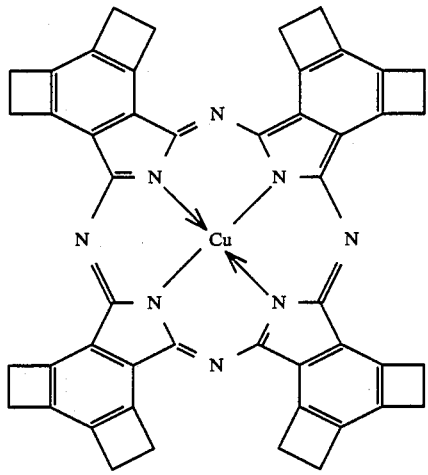 | 2 |
| 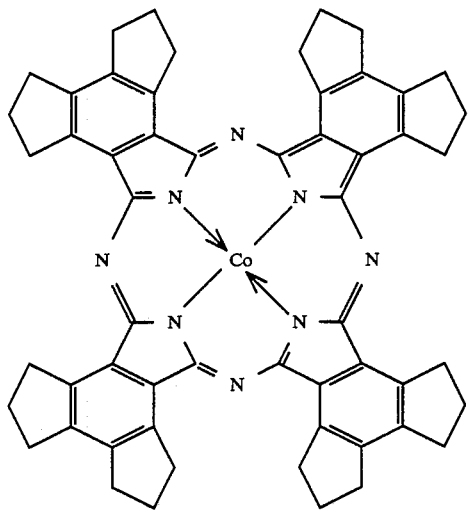 | 3 |
| 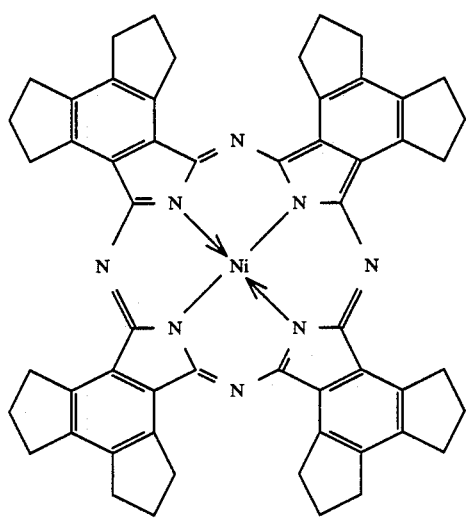 | 4 |

-continued
| | Illustrative Compound No. |
|---|---|
| 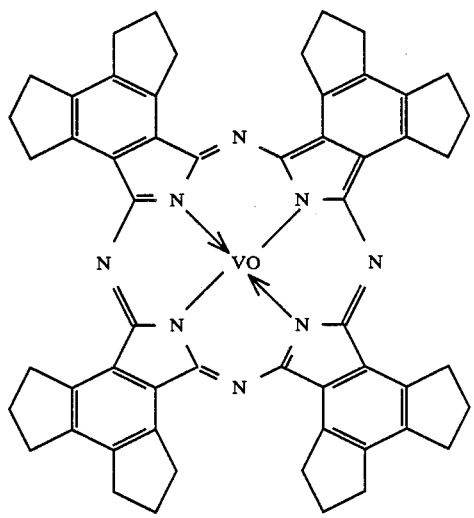 | 5 |
| 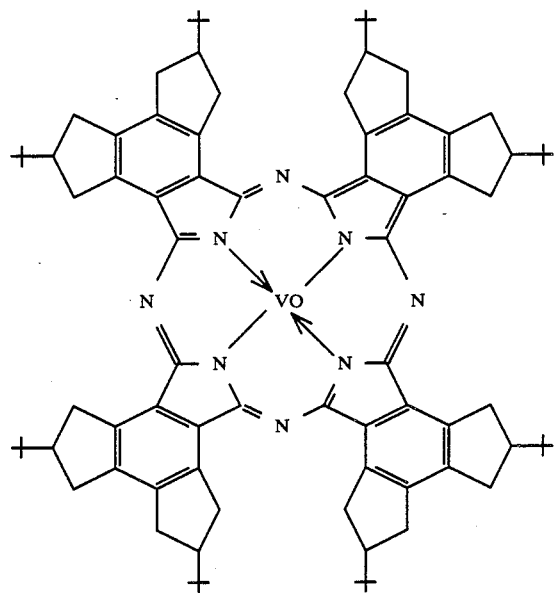 | 6 |

-continued
| | Illustrative Compound No. |
|---|---|
| 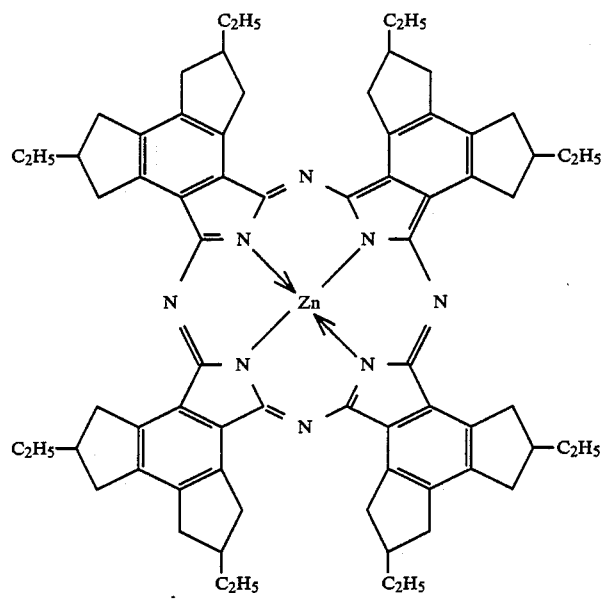 | 7 |
| 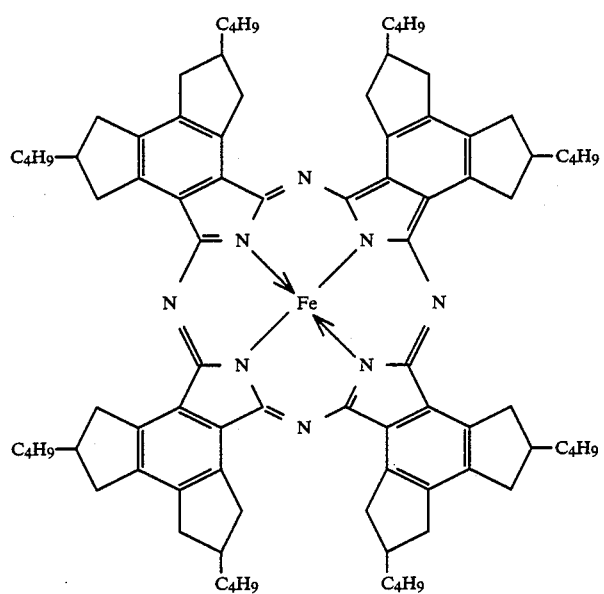 | 8 |

-continued
| | Illustrative Compound No. |
|---|---|
| 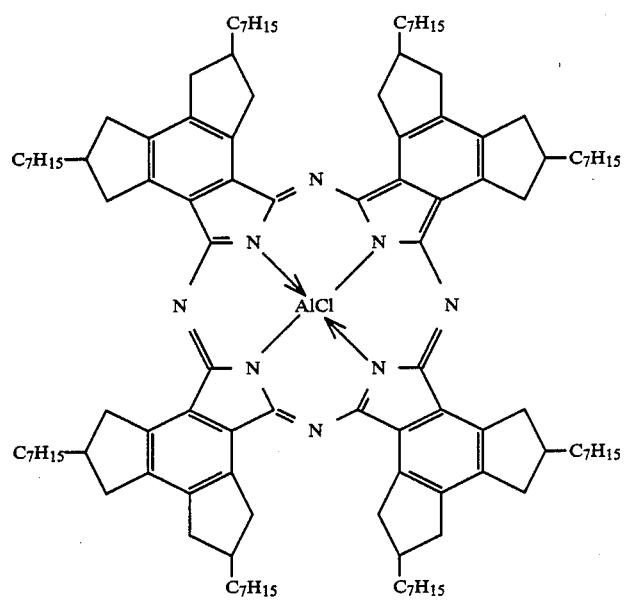 | 9 |
| 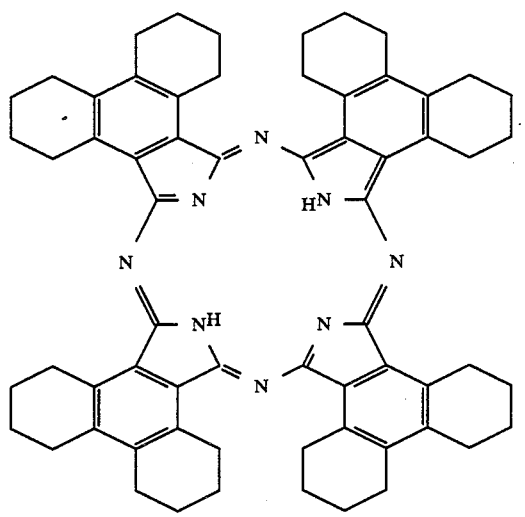 | 10 |

-continued
Illustrative
Compound
No.
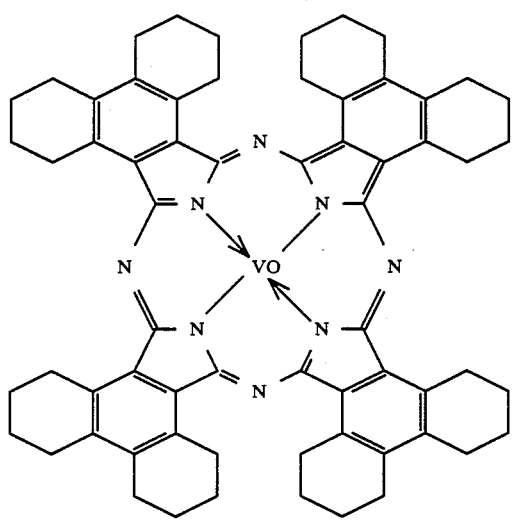
11
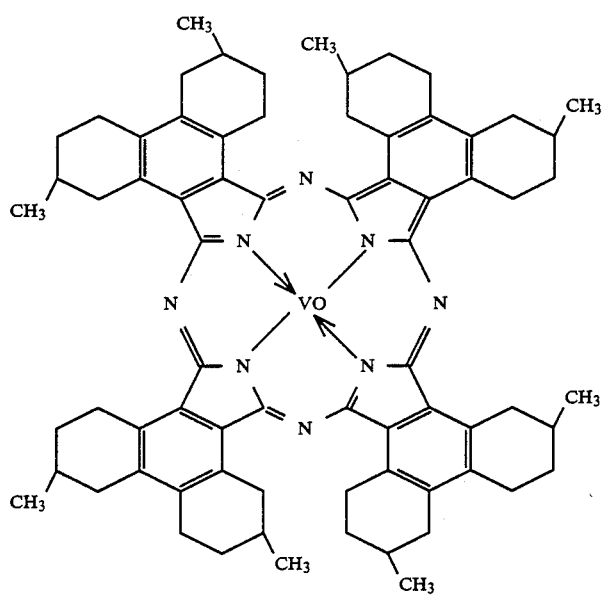
12

-continued
| | Illustrative Compound No. |
|---|---|
| 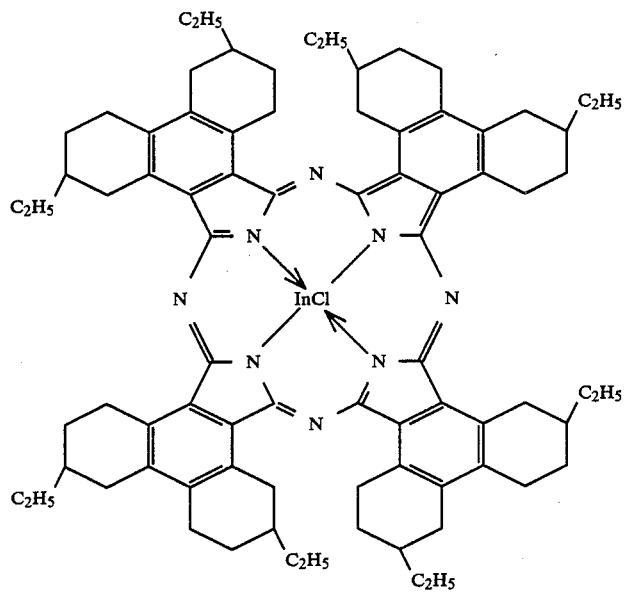 | 13 |
| 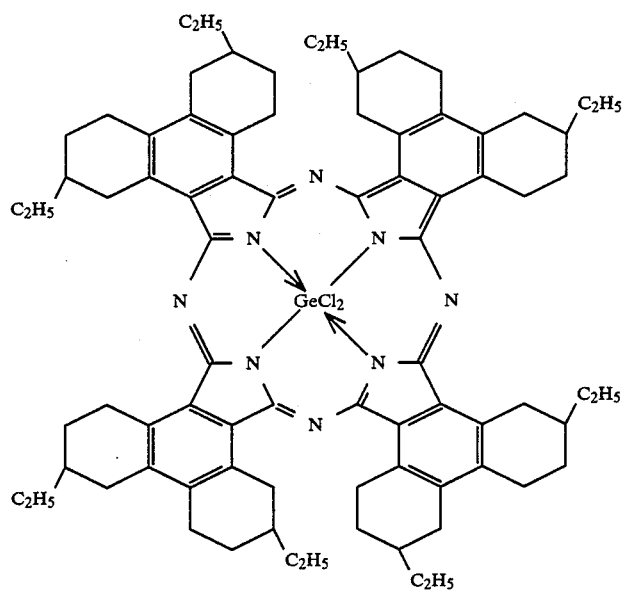 | 14 |

-continued
| | Illustrative Compound No. |
|---|---|
| 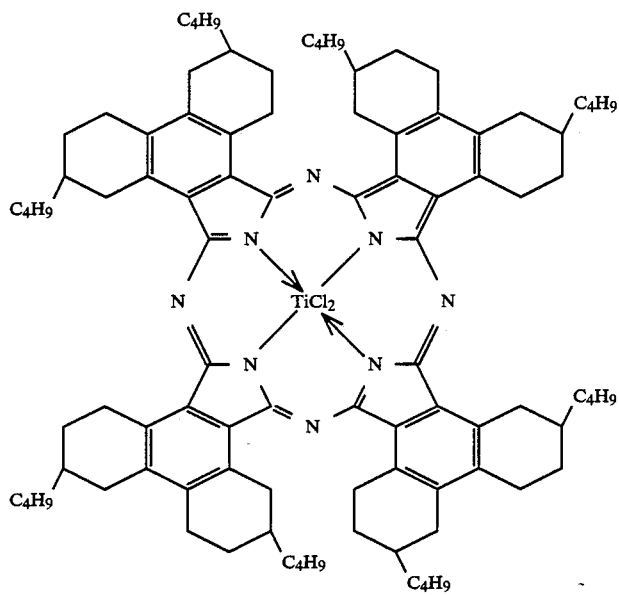 | 15 |
| 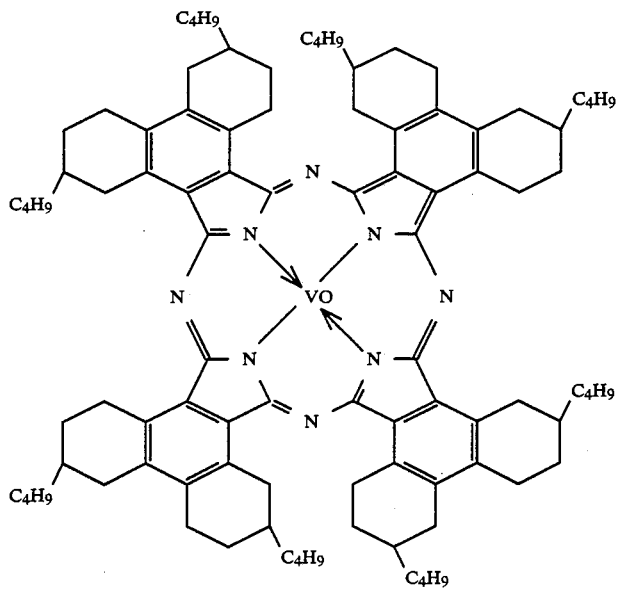 | 16 |

| Illustrative Compound No. |
| --- |
| 17 |
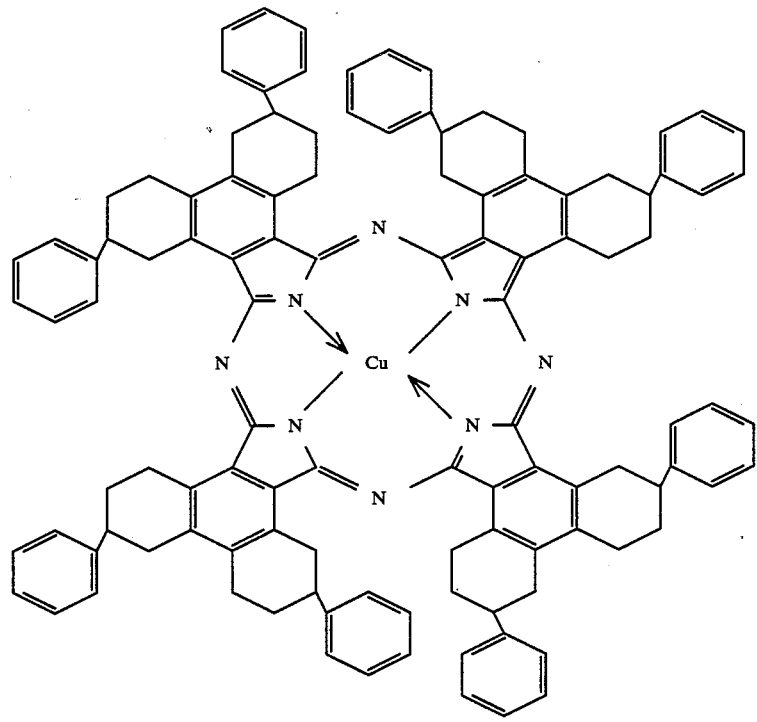
| 18 |
| --- |
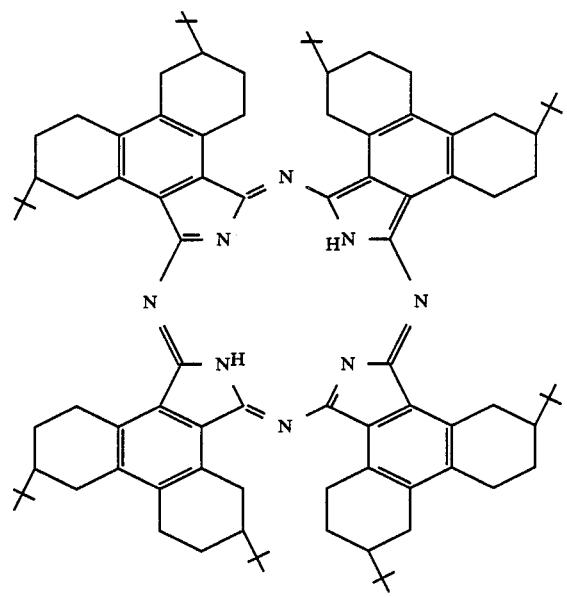

-continued
| | Illustrative Compound No. |
|---|---|
| 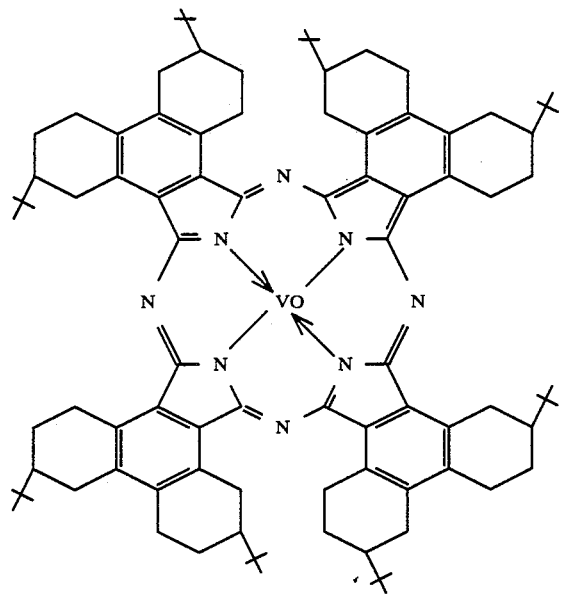 | 19 |
| 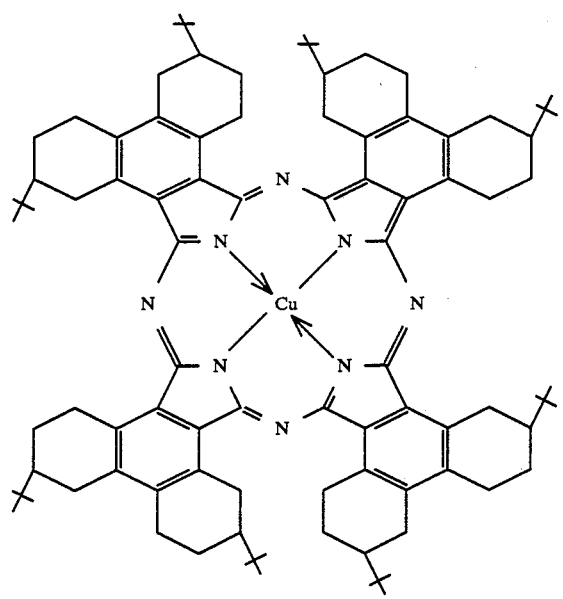 | 20 |

-continued
| | Illustrative Compound No. |
|---|---|
| 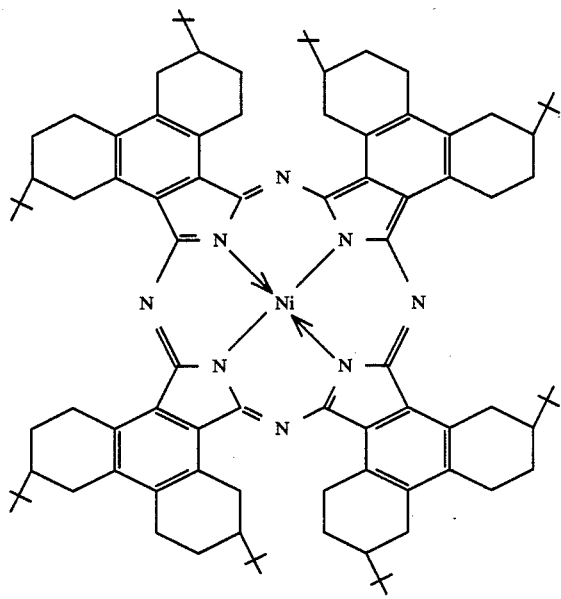 | 21 |
| 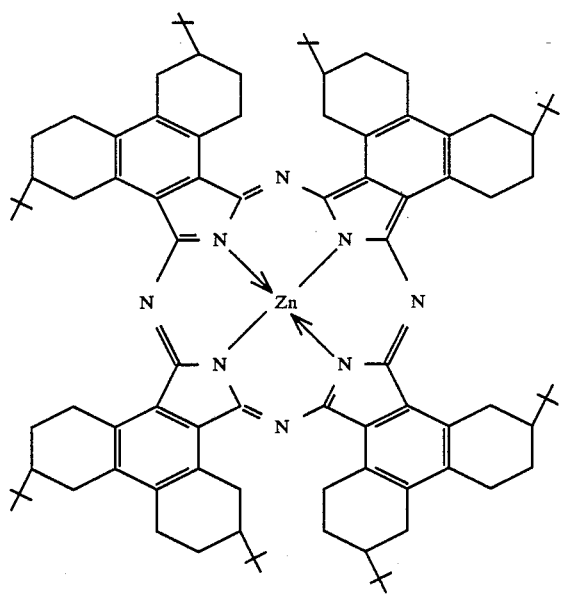 | 22 |

-continued
| | Illustrative Compound No. |
|---|---|
| 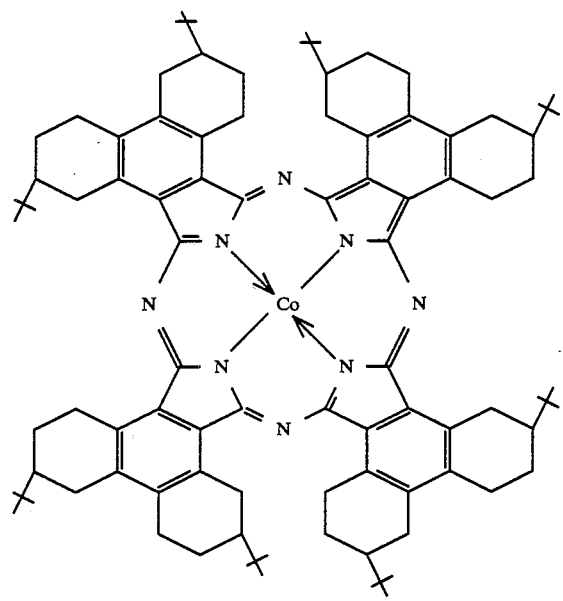 | 23 |
| 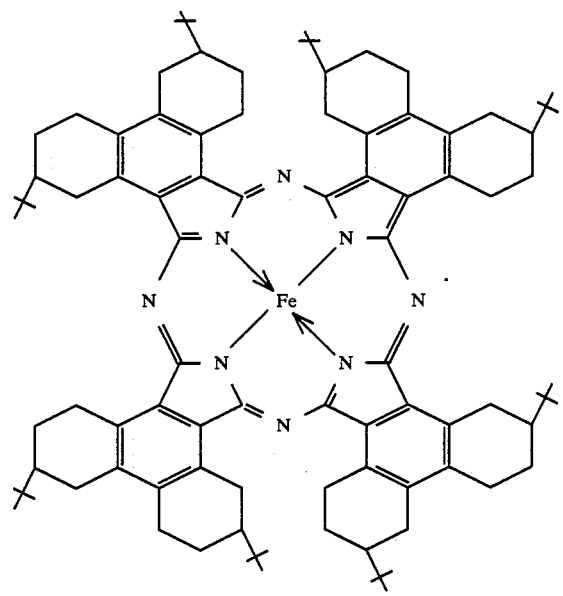 | 24 |

-continued
| | Illustrative Compound No. |
|---|---|
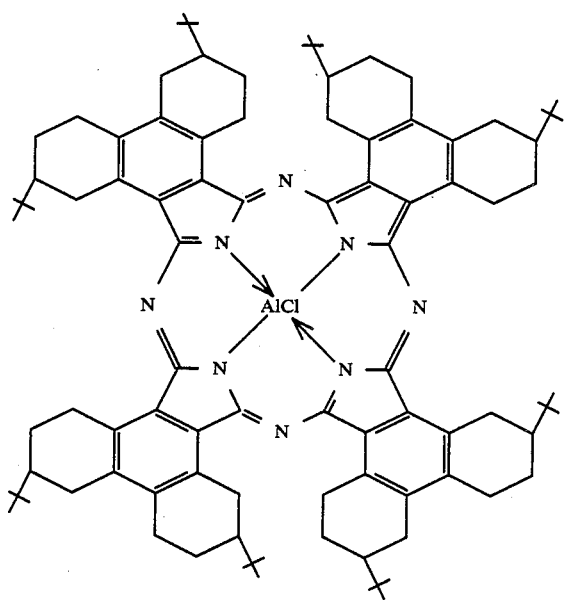
25
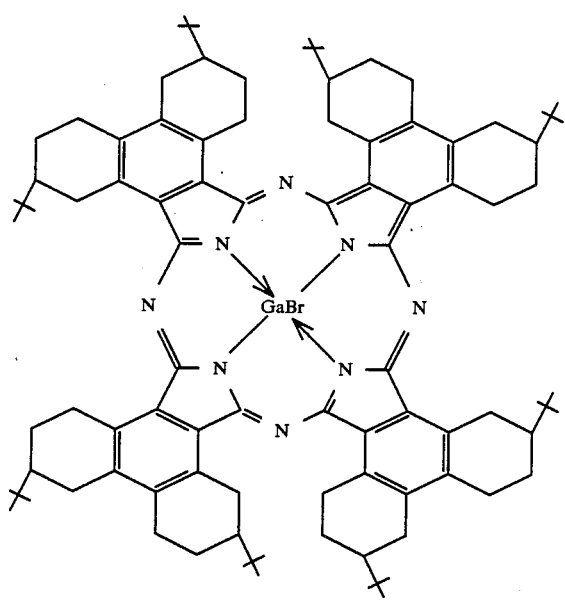
26

-continued
| | Illustrative Compound No. |
|---|---|
| 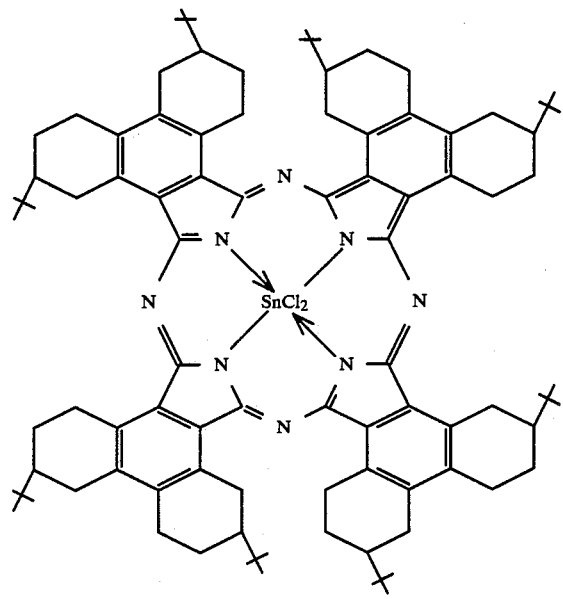 | 27 |
| 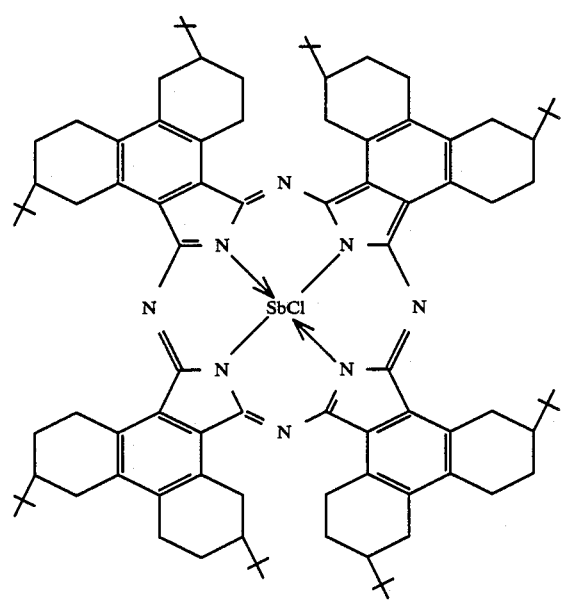 | 28 |

-continued
| Illustrative Compound No. |
| --- |
| 29 |
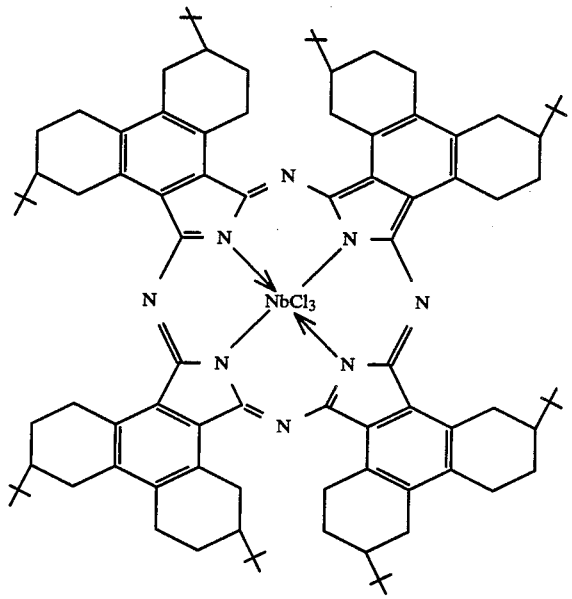
| 30 |
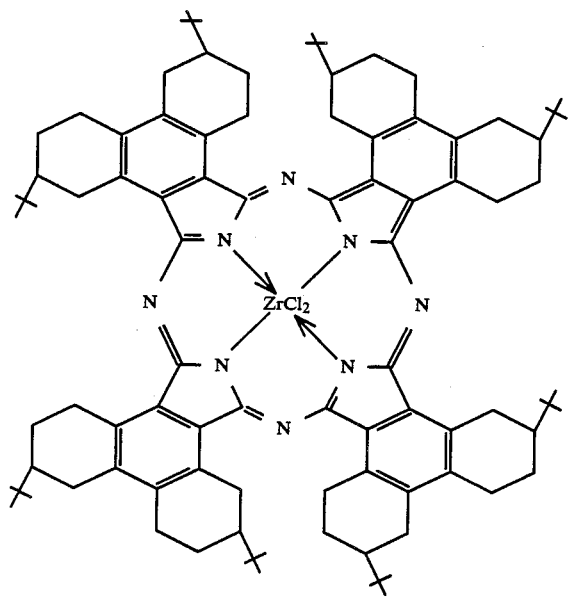

-continued
| | Illustrative Compound No. |
|---|---|
| 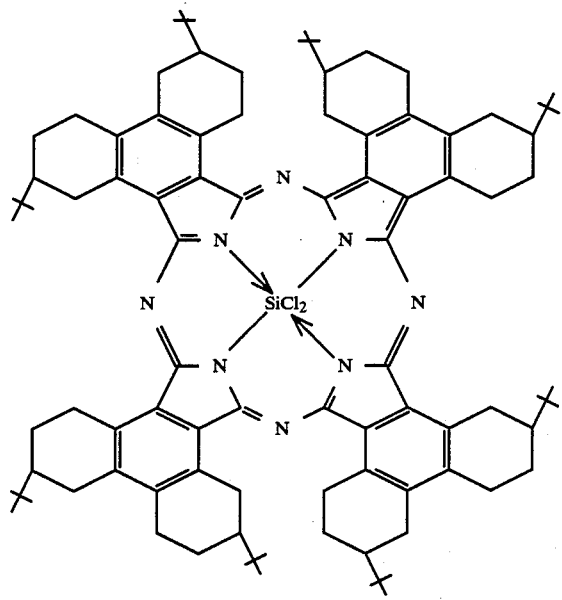 | 31 |
| 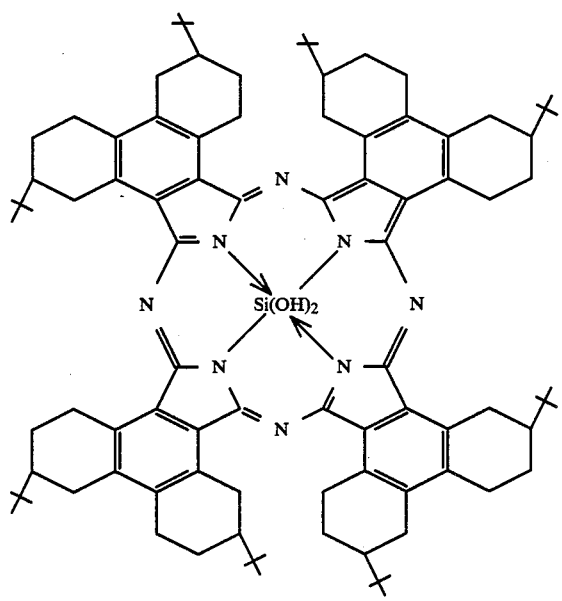 | 32 |

-continued
| Illustrative Compound No. |
|---|
| 33 |
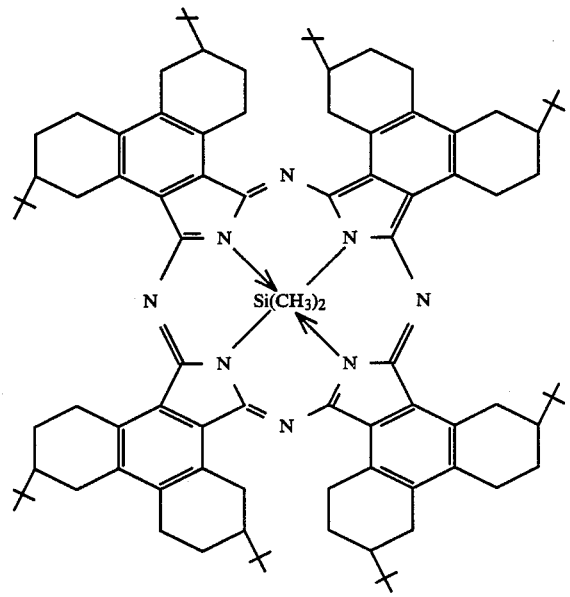
| 34 |
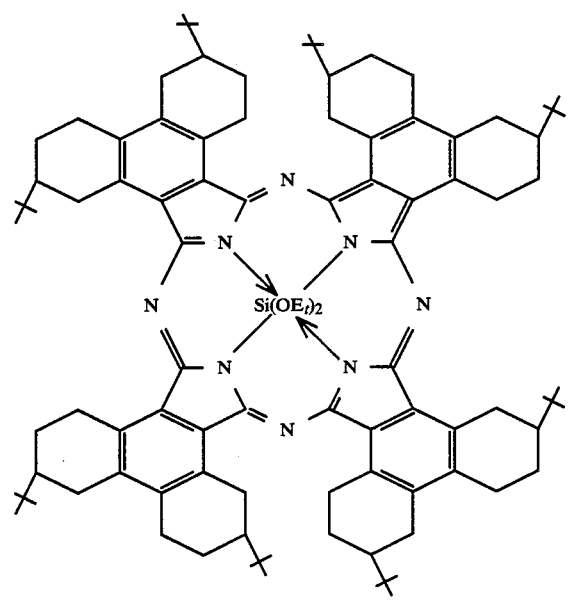

-continued
| | Illustrative Compound No. |
|---|---|
| 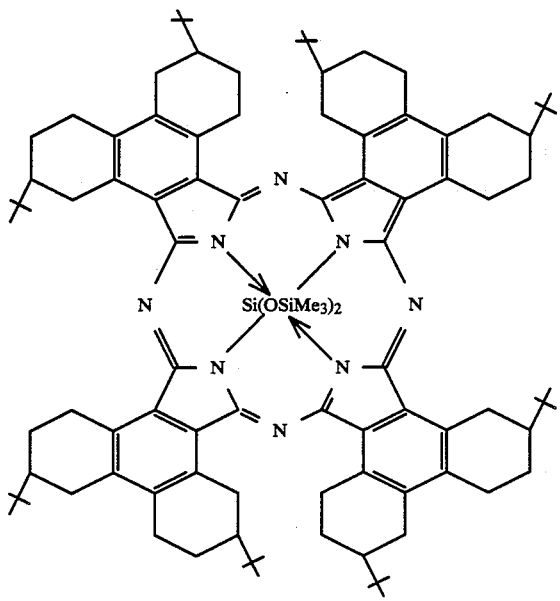 | 35 |
| 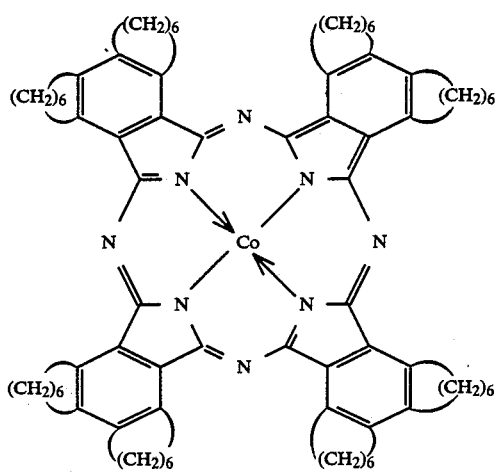 | 36 |
| 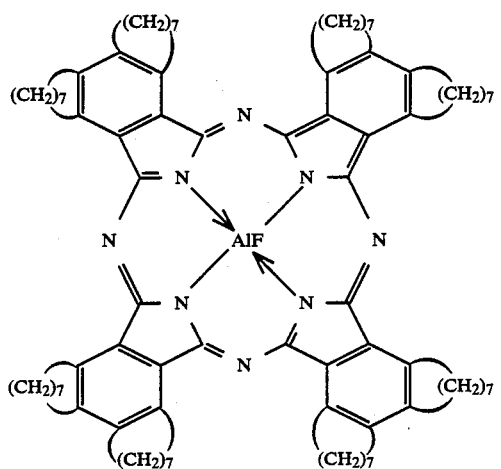 | 37 |

-continued
| | Illustrative Compound No. |
|---|---|
| 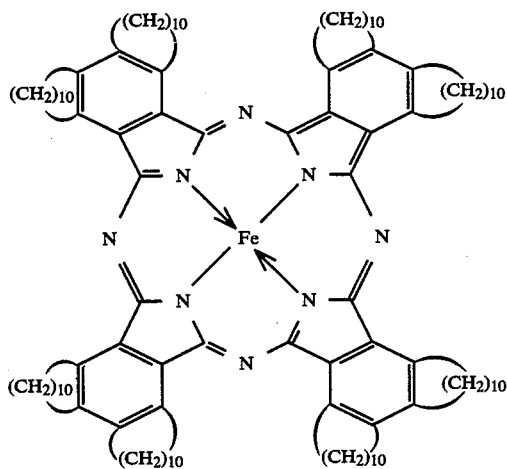 | 38 |
| 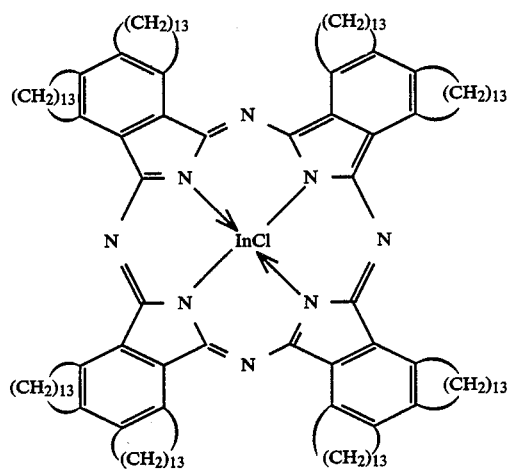 | 39 |
| 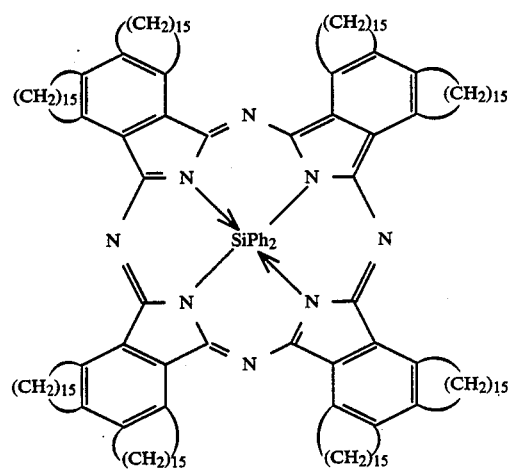 | 40 |

-continued

| Illustrative Compound No. |
|---|
| 41 |

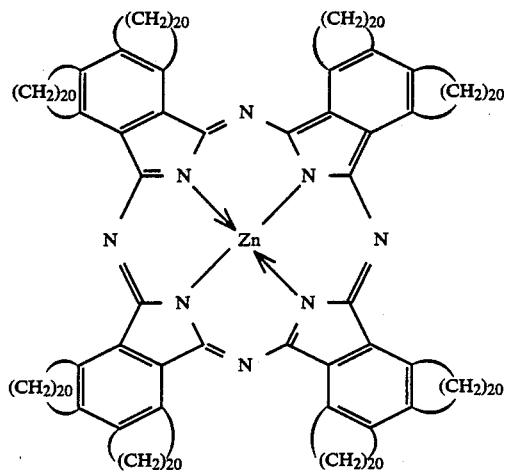

Regarding the optical recording medium according to this invention, an optical disk will be described by way of example in Example 15. Besides, an optical card or optical tape may also be mentioned as such an optical recording medium.

The liquid crystal display panel according to this invention is known as far as its construction is concerned. For example, two substrates are provided in combination with one side of one of the substrates opposing one side of the other substrate. At least one electrode is provided on each of the substrates. Reference is now made to FIG. 1, which illustrates a liquid crystal display panel according to this invention and a hand-writing input light pen to be used in combination with the liquid crystal display panel. The liquid crystal display panel has a structure such that a liquid-crystal material 106 is hermetically sealed between two substrates 102,104 at least one of which is transparent.

The upper substrate 102 carries electrodes (transparent) 108 provided thereon in the pattern of a stripe and the lower substrate 104 has heating electrodes 110 provided also in the pattern of a stripe, whereby both electrode groups thus form an X-Y matrix and their crosspoints serve as individual picture elements. The inner surfaces of the upper and lower substrates, which are brought into contact with the liquid-crystal material, may be subjected to an orientation processing as needed, so that the direction of orientation of molecules of the liquid-crystal material may be determined.

The hand-writing input light pen designated at numeral 112 is internally equipped with a semiconductor laser 114 and a condenser lens unit 116, so that a laser beam 118 emitted from the semiconductor laser 114 and adapted to form near infrared light is focused on and irradiated into the liquid-crystal material 106 through the condenser lens unit 116.

The phthalocyanine compound of this invention, which has been mixed in the liquid-crystal material 106, absorbs the laser beam and gives off heat to raise the temperature of the liquid-crystal material, so that the liquid-crystal material is tentatively transformed into an isotropic liquid phase. In the course of cooling which takes place subsequent to shifting of the light pen 112, regions presenting intense scattering are formed in the liquid-crystal material so that the writing is achieved.

The proportion of the light-absorptive substance represented by the general formula (I) in the liquid-crystal material may preferably be in a range of 0.1–10 wt. % based on the liquid crystal.

Any known liquid-crystal material may be used so long as it is a liquid crystal of the alkylcyano-biphenyl type.

This invention will hereinafter be described specifically by the following examples. It should of course be borne in mind that the subject matter and applicable scope of this invention are not limited by the following examples.

EXAMPLE 1

Preparation of Illustrative Compound No. 19

In 7 ml of α-chloronaphthalene, 1.9 g of 9,10-dicyano-3,7-di-tert-butyl-1,2,3,4,5,6,7,8-octahydrophenanthrene and 0.3 g of vanadium trichloride were heated under reflux for 3 hours. After distilling out the α-chloronaphthalene under reduced pressure, the residue was separated and purified with a 1:1 (by volume) mixture of benzene and n-hexane by chromatography on a silica gel column, thereby obtaining 300 mg of the intended phthalocyanine compound as a dark green solid.

Its elemental analysis data conformed well to the calculated data as $C_{96}H_{128}N_8VO$.

|  | C | H | N |
|---|---|---|---|
| Calculated | 78.92% | 8.83% | 7.67% |
| Found | 78.75% | 8.70% | 7.81% |

Upon measurement of its absorption spectrum in n-hexane, λmax was 744 nm.

EXAMPLE 2

Preparation of Illustrative Compound No. 21

In 10 ml of quinoline, 800 mg of 9,10-dicyano-3,7-di-tert-butyl-1,2,3,4,5,6,7,8-octahydrophenanthrene and 200 mg of nickel chloride were heated under reflux for 8 hours.

After distilling out the quinoline under reduced pressure, the residue was separated and purified with a 1:1 (by volume) mixture of benzene and n-hexane by chromatography on a silica gel column, thereby obtaining 100 mg of the intended phthalocyanine compound as a dark green solid.

Its elemental analysis data conformed well to the calculated data as $C_{96}H_{128}N_8Ni$.

|  | C | H | N |
|---|---|---|---|
| Calculated | 79.37% | 8.88% | 7.71% |
| Found | 79.60% | 8.75% | 7.68% |

Upon measurement of its absorption spectrum in n-hexane, λmax was 702 nm.

EXAMPLE 3

Preparation of Illustrative Compound No. 18

Added to a solution of sodium 1-pentanoate which had been prepared from 2 g of metal sodium and 50 ml of 1-pentanol was 13 g of 9,10-dicyano-3,7-di-tert-butyl-1,2,3,4,5,6,7,8-octahydrophenanthrene, followed by heating under reflux for 3 hours. After distilling out the 1-pentanol, 50 ml of 2N hydrochloric acid was added, followed by a further addition of 200 m; of n-hexane. An organic layer was separated and the n-hexane was then distilled out under reduced pressure. Using a 1:2 by volume mixture of benzene and n-hexane as an eluent, the residue was separated and purified by chromatography on a silica gel so that 3.2 g of the intended phthalocyanine compound was obtained as a green solid.

Its elemental analysis data conformed well to the calculated data as $C_{96}H_{130}N_8$.

|  | C | H | N |
|---|---|---|---|
| Calculated | 82.59% | 9.39% | 9.72% |
| Found | 82.80% | 9.51% | 9.67% |

Upon measurement of its absorption spectrum in n-hexane, λmax was 733 nm.

EXAMPLE 4

Preparation of Illustrative Compound No. 20

In a mixture of 10 ml of N,N-dimethylformamide and 10 ml of ethanol, 200 mg of the phthalocyanine compound prepared in Example 3 and 20 mg of copper acetate were heated under reflux at 100° C. for 3 hours. After distilling out the solvents under reduced pressure, the residue was separated and purified with a 1:1 (by volume) mixture of benzene and n-hexane by chromatography on a silica gel column, thereby obtaining 150 mg of the intended phthalocyanine compound as a dark green solid.

Its elemental analysis data conformed well to the calculated data as $C_{96}H_{128}N_8Cu$.

|  | C | H | N |
|---|---|---|---|
| Calculated | 79.10% | 8.85% | 7.69% |
| Found | 79.32% | 8.80% | 7.55% |

Upon measurement of its absorption spectrum in n-hexane, λmax was 700 nm.

EXAMPLES 5-7

Preparation of Illustrative Compound Nos. 22, 23 and 24

The respective phthalocyanine compounds were separately prepared following the procedure of Example 4 except that zinc acetate, cobalt acetate and iron acetate were used respectively in place of copper acetate.

The compounds thus obtained showed the following maximum absorption wavelengths in their absorption spectra respectively.

| Illustrative Compound No. | λ max in n-hexane |
|---|---|
| 22 | 702 nm |
| 23 | 705 nm |
| 24 | 700 nm |

EXAMPLE 8

Preparation of Illustrative Compound No. 33

In 10 ml of quinoline, 3.5 g of 9,10-dicyano-3,7-di-tert-butyl-1,2,3,4,5,6,7,8,-octahydrophenanthrene, 0.5 g of dimethylchlorosilane and 0.5 g of ammonium molybdate were dissolved. They were reacted for 1 hour under heating and reflux. After distilling out the quinoline under reduced pressure, the residue was separated and purified with a 1:1 (by volume) mixture of benzene and n-hexane by chromatography on a silica gel column, thereby obtaining 500 mg of the intended phthalocyanine compound as a green solid.

Its elemental analysis data conformed well to the calculated data as shown below.

|  | C | H | N |
|---|---|---|---|
| Calculated | 81.05% | 9.30% | 7.72% |
| Found | 81.24% | 9.37% | 7.70% |

Upon measurement of its absorption spectrum in n-hexane, λmax was 720 nm.

EXAMPLES 9-13

Preparation of Illustrative Compound No. 11, 12 16, 5 and 6

The respective phthalocyanine compounds were separately prepared following the procedure of Example 1 except that 9,10-dicyano-1,2,3,4,5,6,7,8-octahydrophenanthrene, 9,10-dicyano-3,7-dimethyl-1,2,3,4,5,6,7,8-octahydrophenanthrene, 9,10-dicyano-3,7-dibutyl-1,2,3,4,5,6,7,8-octahydrophenanthrene, 4,5-dicyano-1,2,3,6,7,8-hexahydro-as-indacene and 4,5-dicyano-2,7-di-tert-butyl-1,2,3,6,7,8-hexahydro-asindacene instead of 9,10-dicyano-3,7-di-tert-butyl-1,2,3,4,5,6,7,8-octahydrophenanthrene.

The compounds thus obtained showed the following maximum absorption wavelengths in their absorption spectra respectively.

| Illustrative Compound No. | λ max in benzene |
|---|---|
| 11 | 714 nm |
| 12 | 714 nm |
| 16 | 714 nm |
| 5 | 714 nm |
| 6 | 714 nm |

EXAMPLE 14

The phthalocyanine compound prepared in Example 1 and the following compound,

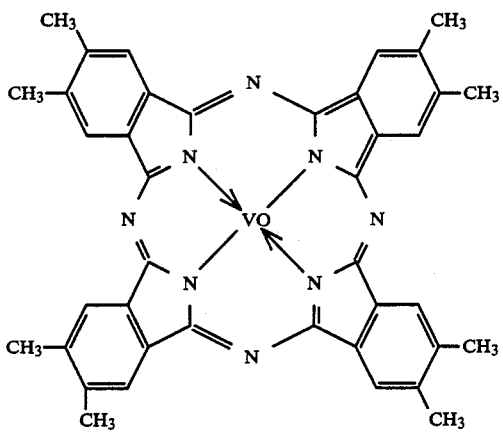

as a comparative substance were separately dissolved at room temperature in 1 l of n-hexane to investigate their solubilities. Results are shown in Table 1.

TABLE 1

| Compound | Solubility (g/l) |
| --- | --- |
| Compound of Example 1 | at least 30 g |
| Comparative substance | at most 0.5 g |

EXAMPLE 15

A $2 \times 10^{-2}$ M/l solution was prepared from the phthalocyanine compound prepared in Example 1 and n-octane. A transparent substrate of a polycarbonate disk having a diameter of 30 cm and a thickness of 1.2 mm was spin-coated at 1,000 rpm with the solution. After drying, the thickness of the resultant pigment coating film was measured. It was 0.08 μm. The reflectivity at the absorption maximum of 780 nm was The term "reflectivity" as used herein means 5° regular reflectivity as measured from the side of the pigment film by using an aluminum plate as a reference.

While rotating the thus-fabricated recording disk at 600 rpm, pits were formed in the pigment film by using laser diode beams of 780 nm. When the numerical aperture was set at 0.6 at this time, the actual output required to focus the beams on the medium was 9 mW. The beams were modulated by constant tone signals ("carriers"). The pits were thereafter read out by using laser beams having the same wavelength but an output reduced to 1 mW, whereby the carrier-to-noise (C/N) ratio was measured. It was 57 dB.

EXAMPLE 16

In the above-described liquid crystal display device of FIG. 1 which was composed of the liquid crystal display panel and the light pen having the near infrared light source, a liquid-crystal material and a light-absorptive substance were hermetically sealed within the liquid crystal display panel.

As the liquid-crystal material designated at numeral 106, a liquid crystal of the alkyl cyanobiphenyl type represented by the general formula:

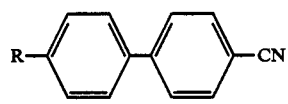

Figure 2:
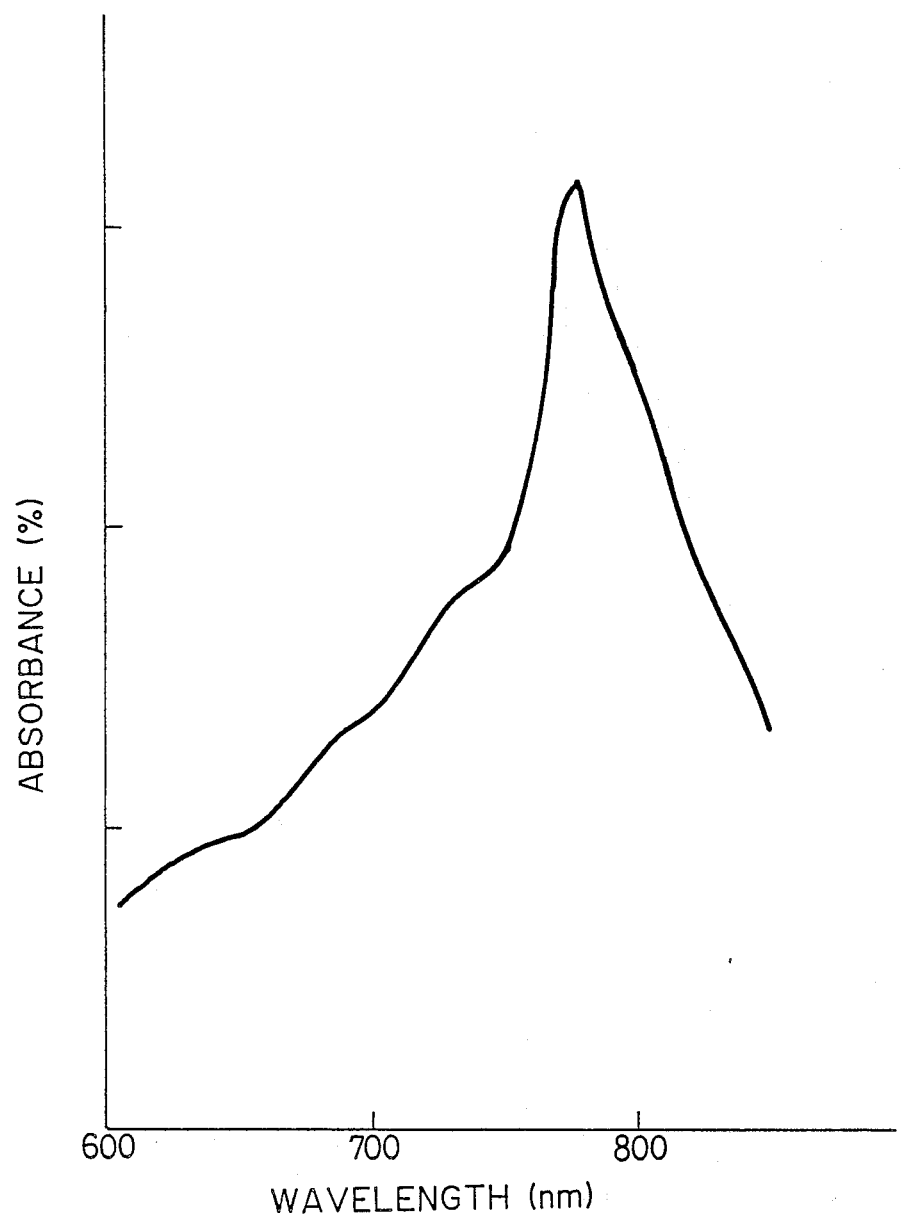
FIG. 2 is a diagrammatic representation showing light absorption characteristics of a liquid-crystal material employed in the liquid crystal display panel.

(R: alkyl) was used. That liquid crystal was mixed with 0.7 wt. % of the compound prepared in Example 1. The liquid-crystal material 106 transformed at 37° C. from a smectic phase into a nematic phase and further at 42° C. into an isotropic liquid phase. The light absorption characteristics of the liquid-crystal material 106 containing the light-absorptive substance are as shown in FIG. 2. The peak of its absorbance conformed well to the wavelength of the semiconductor laser beam provided inside the light pen 112, namely, 780 nm which is one of the wavelengths of semiconductor laser beams employed routinely, i.e., 780 nm and 830 nm.

The following two liquid crystal display panels A,B were fabricated in order to compare the writing characteristics of the liquid-crystal material 106 (mixed with 0.7 wt. % of the light-absorptive substance) in this Example with those of the conventional liquid crystal (without the light-absorptive substance). The liquid crystal display panel A is a liquid crystal display panel fabricated in accordance with a conventional technique. On heating electrodes, a thin film C was deposited as a heat-absorbing member to a thickness of 1,500 Å by vacuum evaporation. The liquid crystal was not added with any light-absorptive substance.

On the other hand, the liquid crystal display panel B is a liquid crystal display panel according to this invention. Thin Al films deposited to a thickness of about 3,000 Å by vacuum evaporation were used as heating electrodes. Neither absorption of light nor generation of heat occur practically by the heating electrodes. The liquid-crystal material employed in the liquid crystal display panel B was a mixture of the liquid crystal employed in the liquid crystal display panel A and 0.7 wt. % of the above-described light-absorptive substance.

In each of the liquid crystal display panels, the thickness of the liquid crystal layer was 10 μm.

Figure 3:
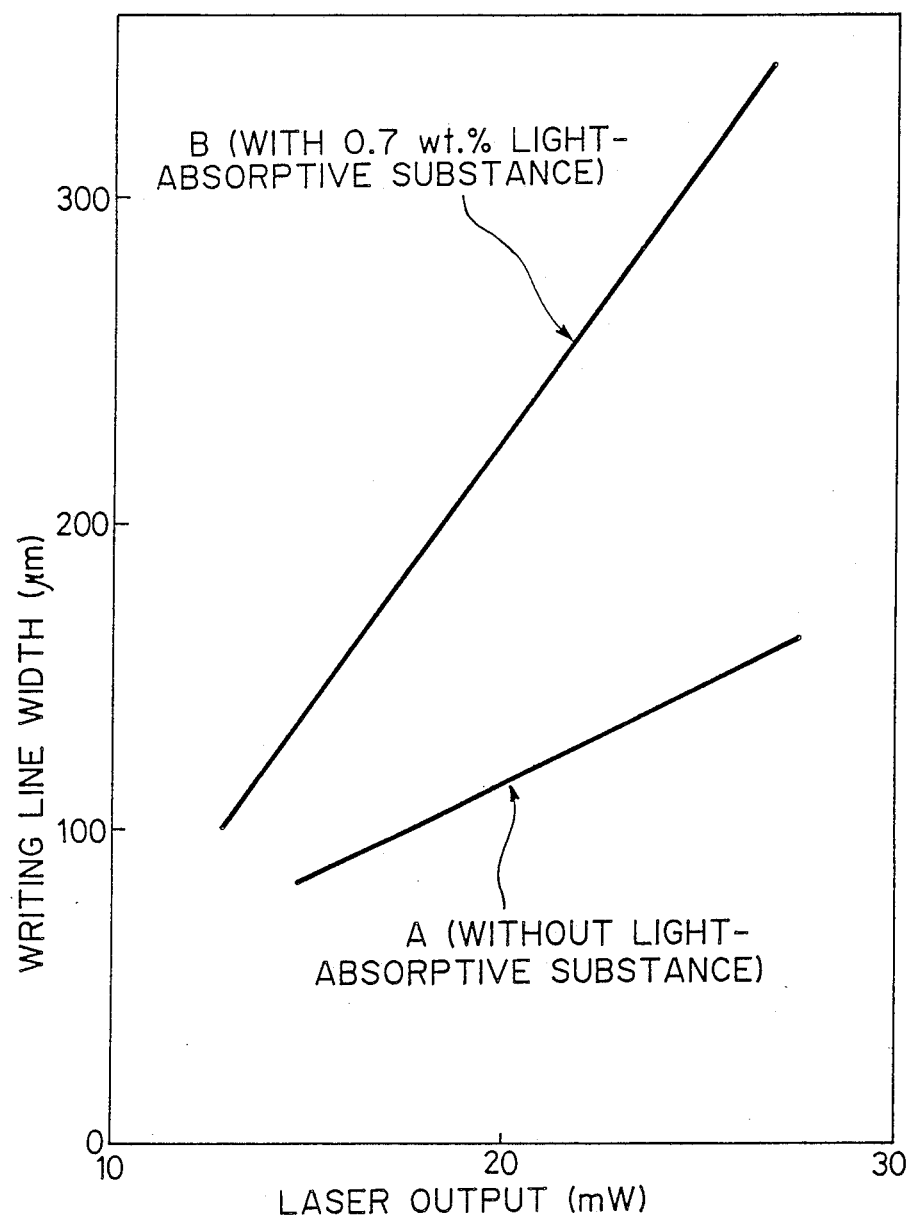
FIG. 3 is a diagrammatic representation depicting writing characteristics of the liquid-crystal material.

Using the light pen, writing was performed on the liquid crystal display panels A,B. Characteristics as shown in FIG. 3 were obtained. Namely, FIG. 3 shows the relationship between laser outputs and the widths of lines drawn when the moving speed of the light pen was set at 0.1 cm/sec. It is envisaged from FIG. 3 that the liquid crystal display panel B according to this invention can give a thicker writing line width compared with the conventional liquid crystal display panel A. The liquid crystal display panel B allowed to draw lines of 160 μm thick at a pen moving speed of 2 cm/sec when the laser output was 20 mW. Namely, it is envisaged that thick lines can still be drawn even when the moving speed of the light pen is increased.

The above-described light-absorptive substance was found to be soluble up to about 2 wt. % in the liquid crystal of the alkyl cyanobiphenyl type. By various weatherability tests, the light-absorptive substance was also found to have very good service life.

Namely, the liquid-crystal material 106 was filled in a capsule and left over for 100 hours under direct exposure to sunlight. Changes in its absorbance and absorption spectrum were then investigated. No changes were observed, so that it was found to be very stable.

We claim:

1. A phthalocyanine compound represented by the following general formula (I):

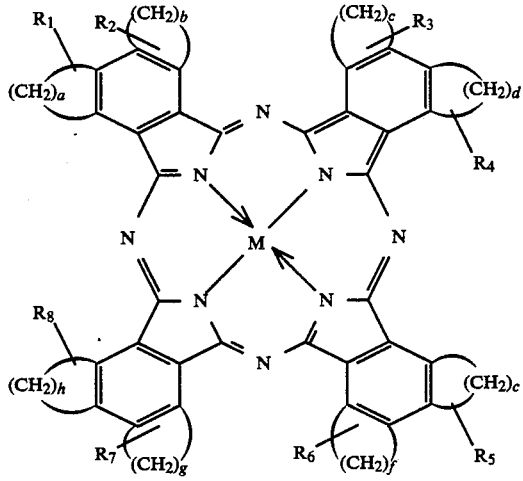

wherein $R_1$–$R_8$ are individually a hydrogen atom or an alkyl or aryl group, a–h stand individually for an integer of 1–20, and M denotes two hydrogen atoms or a metal atom, metal halide, metal oxide, metal hydroxide, dialkylmetal, diarylmetal, bis(alkyloxy)metal or bis(trialkylsilyloxy)metal and wherein alkyl has 1 to 7 carbon atoms and aryl is phenyl.

2. An optical recording medium comprising at least one phthalocyanine compound represented by the following general formula (I):

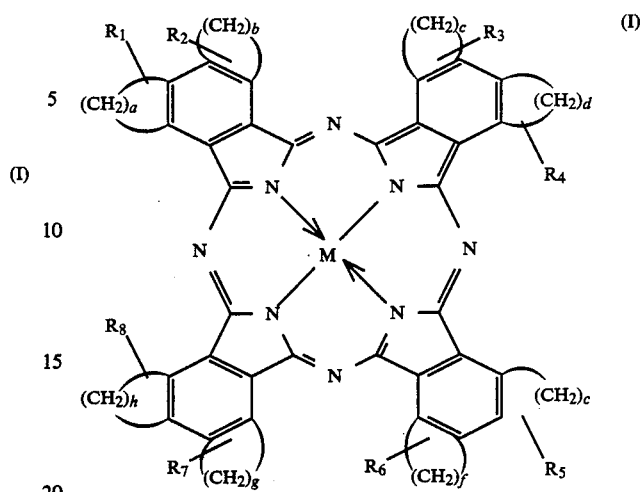

wherein $R_1$–$R_8$ are individually a hydrogen atom or an alkyl or aryl group, a–h stand individually for an integer of 1–20, and M denotes two hydrogen atoms or a metal atom, metal halide, metal oxide, metal hydroxide, dialkylmetal, diarylmetal, bis(alkyloxy)metal or bis(trialkylsilyloxy)metal and wherein alkyl has 1 to 7 carbon atoms and aryl is phenyl.

3. In a liquid crystal display panel composed of two substrates provided in combination with one side of one of said two substrates opposing one side of the other substrate, at least one electrode provided on each of the substrates and a liquid-crystal material having thermooptical effects or electro- and thermooptical effects and sealed between said two substrates, the improvement wherein said liquid-crystal material comprises at least one phthalocyanine compound represented by the following general formula (I):

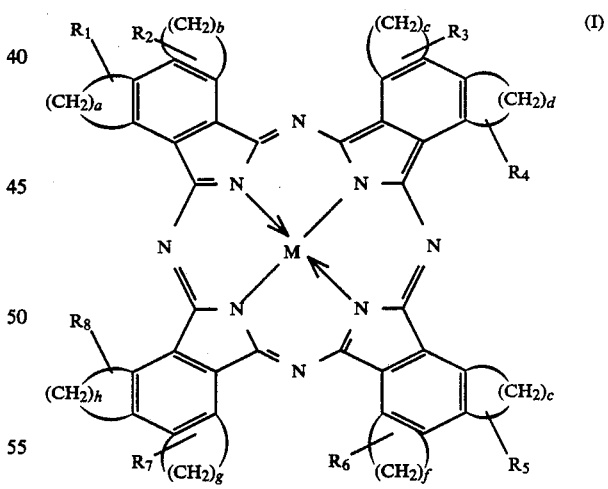

wherein $R_1$–$R_8$ are individually a hydrogen atom or an alkyl or aryl group, a–h stand individually for an integer of 1–20, and M denotes two hydrogen atoms or a metal atom, metal halide, metal oxide, metal hydroxide, dialkylmetal, diarylmetal, bis(alkyloxy)metal or bis(trialkylsilyloxy)metal and wherein alkyl has 1 to 7 carbon atoms and aryl is phenyl.

* * * * *

UNITED STATES PATENT AND TRADEMARK OFFICE
CERTIFICATE OF CORRECTION

Page 1 of 2

PATENT NO. : 4,970,021

DATED : NOVEMBER 13, 1990

INVENTOR(S) : MASAKATSU NAKATSUKA ET AL

It is certified that error appears in the above-identified patent and that said Letters Patent is hereby corrected as shown below:

On the Title page, item [57]
In the Abstract, delete formula (1) in its entirety and replace with new formula (1)

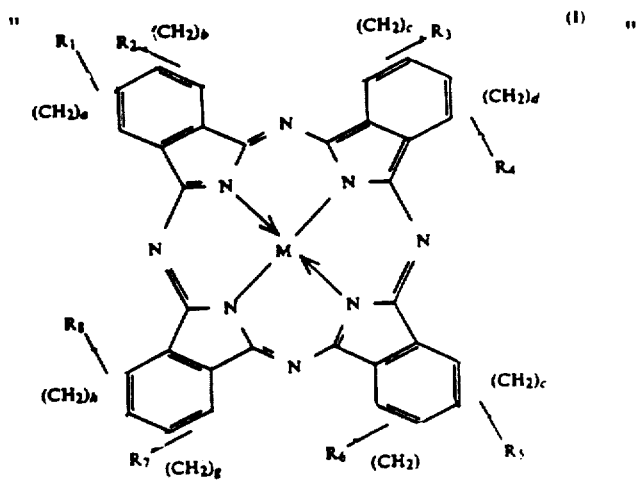

UNITED STATES PATENT AND TRADEMARK OFFICE
CERTIFICATE OF CORRECTION

PATENT NO. : 4,970,021
DATED : November 13, 1990
INVENTOR(S) : Masakatsu Nakatsuka, et. al.

It is certified that error appears in the above-indentified patent and that said Letters Patent is hereby corrected as shown below:

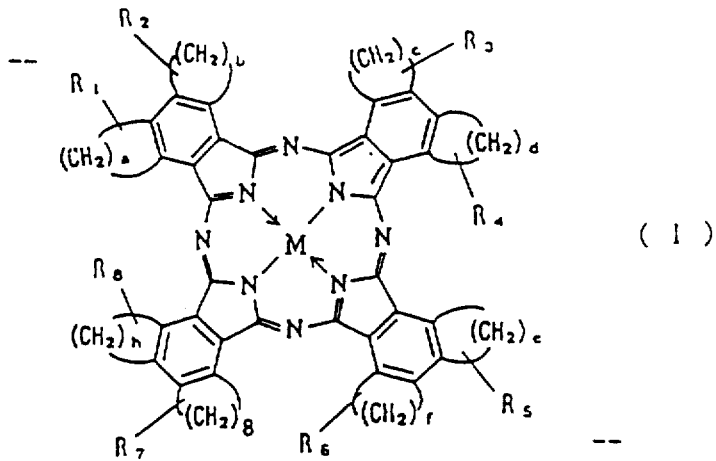

Signed and Sealed this

Nineteenth Day of October, 1993

Attest:

BRUCE LEHMAN

Attesting Officer

Commissioner of Patents and Trademarks